United States Patent [19]

Fock et al.

[11] Patent Number: 5,057,579

[45] Date of Patent: Oct. 15, 1991

[54] POLYACRYLATE ESTERS WITH QUATERNARY AMMONIUM GROUPS

[75] Inventors: Jürgen Fock, Düsseldorf; Dietmar Schaefer; Eberhard Esselborn, both of Essen, all of Fed. Rep. of Germany

[73] Assignee: Th. Goldschmidt AG, Fed. Rep. of Germany

[21] Appl. No.: 448,169

[22] Filed: Dec. 8, 1989

[30] Foreign Application Priority Data

Dec. 15, 1988 [DE] Fed. Rep. of Germany ....... 3842202

[51] Int. Cl.$^5$ ................................................ C08F 8/30
[52] U.S. Cl. ............................... 525/329.5; 525/330.5; 525/330.6; 525/353; 525/359.5; 525/359.6; 525/380
[58] Field of Search ................ 525/329.5, 330.5, 330.6

[56] References Cited

U.S. PATENT DOCUMENTS

| | | | |
|---|---|---|---|
| 2,915,481 | 12/1959 | Ayers et al. | 525/380 |
| 3,418,395 | 12/1968 | Taniguchi et al. | 525/380 |
| 4,391,721 | 7/1983 | Pappas | 525/329.5 |

Primary Examiner—Bernard Lipman
Attorney, Agent, or Firm—Toren, McGeady & Associates

[57] ABSTRACT

Polyacrylate esters with quaternary ammonium groups are disclosed. The esters are obtained by transesterifying alkyl polyacrylate esters with dialkylaminoalkanols, followed by quaternization.

The polymers are free of physiologically questionable components and can therefore be used for the preparation of cosmetic products, preferably for hair cosmetics. The polymers furthermore are suitable for finishing fibers or of textile products.

The invention is furthermore directed to polyacrylate esters with tertiary amino groups, which are formed as intermediates in the preparation of polyacrylate esters with quaternary ammonium groups.

4 Claims, No Drawings

POLYACRYLATE ESTERS WITH QUATERNARY AMMONIUM GROUPS

FIELD OF INVENTION

The invention is directed to polyacrylate esters with quaternary ammonium groups and their use in cosmetic preparations, particularly in preparations for the care of hair and as textile auxiliaries, particularly for the antistatic finishing of textile fibers and flat or planar textile products.

Considered from a different aspect, the invention is concerned with polyacrylate esters with tertiary amino groups.

BACKGROUND INFORMATION AND PRIOR ART

Polyacrylate esters with quaternary ammonium groups are known and are used as cationic auxiliaries, especially to flocculate solid particles in sewage (European published application 176,757), for the antistatic finishing of textile fibers (German Offenlegungsschrift 2,242,914), to improve the dyeability of wool and to produce electrically conducting duplicating paper or as hair setting lotion (German Offenlegungsschrift 2,423,182).

The known polyacrylate esters with quaternary ammonium groups are synthesized, according to the state of the art, by the copolymerization of acrylate esters, especially methyl acrylates and acrylate ester derivatives, which have quaternary ammonium groups.

As acrylate ester derivatives with quaternary ammonium groups, compounds such as (meth)acryloyloxyethyl- or (meth)acryloyloxypropyltrialkyl- or -dialkylbenzylammonium halides are used, the alkyl groups having, in particular, 1 to 3 carbon atoms. In addition, other monomers, such as styrene, methyl-, ethyl-, butyl- and/or dodecyl (meth)acrylate, vinyl acetate, vinyl propionate, N-vinylpyrrolidone, acrylamide and/or acrylonitrile can be copolymerized.

The free radical copolymerization of the aforementioned monomers results in polymers with a very wide distribution of molecular weights. The molecular weight distribution curve accordingly is relatively flat and, moreover, has two or more maxima, which indicate that the polymerization product is relatively heterogeneous. It may be assumed that the reason for this lies in the copolymerization parameters of the individual monomers, which deviate considerably from the ratio of 1, and is the result particularly of the ionic character of the monomers with quaternary ammonium groups.

It has, moreover, been ascertained that moieties which are physiologically questionable and may also have toxic properties, are contained in the polymers obtained by copolymerization. It may be assumed that these unwanted properties can be ascribed to the low molecular weight moieties of the polymer. The removal of these fractions or moieties from the polymer in an economical manner is not possible. For many applications, however, especially in cosmetics, the physiological safety of products is an imperative prerequisite for their usability. It is therefore of particular interest to prepare polyacrylate esters with quaternary ammonium groups, which are free of physiologically questionable components.

The use of an anionic polymerization method, similar to that described in the German Offenlegungsschrift 2,262,588 for the synthesis of acrylate polymers with a molecular weight of 500 to 5,000, does not represent a usable solution for the aforementioned objective. The danger that the reaction products will gel, is high. Moreover, the conversion of an anionic polymerizing method to an industrial scale is also beset with problems that are related to safety.

OBJECT OF THE INVENTION

It is therefore an object of the invention to prepare polyacrylate esters with quaternary ammonium groups, which are to contain the smallest possible amounts of low molecular weight products and be physiologically safe.

It is also an object of the invention to provide polyacrylate esters with tertiary amino groups which are useful as intermediates in the preparation of the esters with quaternary ammonium groups.

SUMMARY OF THE INVENTION

It has been ascertained that polymers, which contain only small amounts or moieties of low molecular weight products, are obtained by the transesterification of suitable polyacrylate esters with selected aminoalcohols. As intermediates in this reaction, acrylate esters with tertiary amino groups are formed, which can be converted by quaternization into the desired polyacrylate esters with quaternary ammonium groups.

The invention therefore provides for polyacrylate esters with quaternary ammonium groups, which are the transesterification product of alkyl polyacrylate esters, obtained by free radical polymerization and the alkyl groups of which contain 1 to 8 carbon atoms, with compounds of the general formula

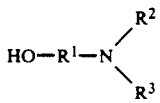

wherein
$R^1$ is a bivalent group of the general formula

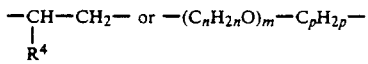

$R^4$ is hydrogen or an alkyl group with 1 to 16 carbon atoms,
$n = 2$, 3 or 4,
$m = 1$ to 20,
$p = 2$, 3 or 4
$R^2$, $R^3$ are alkyl groups with 1 to 18 carbon atoms, the reactants being employed in such amounts that up to 70% of the ester groups are transesterified. The transesterification is performed in the presence of a known transesterification catalyst at temperatures from 70° to 140° C., optionally in the presence of a solvent. A mixed polyacrylate ester with tertiary amino groups is thus formed as an intermediate. This intermediate is subsequently subjected to quaternization with alkyl or alkylaryl halides of the general formula $R^5X$ wherein
$R^5$ is an alkyl group with 1 to 4 carbon atoms or a benzyl group, while X is a halogen atom, or with dimethyl or diethyl sulfate, in a known manner at temperatures from 20° to 140° C. and, if necessary, at an elevated pressure.

In the aminoalcohol of formula I, $R^1$ is a bivalent group of the formula

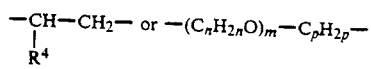

Examples of such groups are

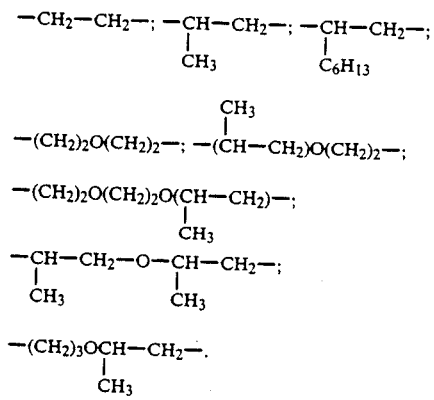

Particularly preferred are groups, in which $R^4$ is a hydrogen, methyl or ethyl group. For the ether groups, those are preferred, in which n and p have a value of 2 or 3. On the other hand, m preferably has a value of 1 to 10

$R^2$ and $R^3$ are alkyl groups with 1 to 18 carbon atoms. The alkyl groups may be linear or branched. Preferred are alkyl groups with 1 to 6 carbon atoms. Particularly preferred are alkyl groups with 1 to 4 carbon atoms, such as the methyl, ethyl, propyl, isopropyl, butyl and isobutyl group.

Within the polymeric molecule, the groups, superscripts and subscripts may have different meanings or values, so that the subscripts in the average polymer molecule may also assume fractional values.

For the transesterification, alkyl polyacrylate esters are used, the alkyl groups of which have 1 to 8 carbon atoms. Preferably, alkyl esters are used, the alkyl group of which has 1 to 4 carbon atoms. The selection of the methyl, ethyl or butyl esters of the polyacrylic acid for the transesterification is therefore especially preferred.

The transesterification of the polyacrylate esters with the dialkylaminoalcohols is carried out in a known manner. Advantageously, it takes place in the presence of known transesterification catalysts, such as alkyl titanates or alkali alcoholates and, if necessary, in the presence of a solvent, such as toluene, xylene or a hydrocarbon fraction having a boiling point range from 80° to 160° C. The solvent serves primarily to carry the alcohol, released during the transesterification, out of the reaction mixture. The solvent used thus limits the transesterification temperatures, which should lie between 70° and 140° C.

The transesterification reaction should be conducted at such quantitative ratios, that up to 70%, preferably 5 to 50% and particularly 20 to 50% of the alkyl esters are transesterified.

A polyacrylate ester with tertiary amino groups is obtained as intermediate. These compounds have their own utility since they can also be used in the area of textile auxiliaries and in the cosmetic area, particularly for hair cosmetics.

In a second step, the above intermediate is quaternized, also in a known manner, with alkyl or alkylaryl halides or dimethyl or diethyl ether sulfate.

As alkyl or alkylaryl halides, those of the general formula $R^5X$ are used, $R^5$ being an alkyl group with 1 to 4 carbon atoms or a benzyl group and X a halogen group. Examples of such halogen compounds are methyl chloride, ethyl chloride, butyl chloride, methyl bromide or ethyl bromide.

The quaternization takes place at temperatures from 20° to 140° C., depending on the boiling point of the quaternizing agent used. If necessary, the quaternization is carried out in a closed system at an elevated pressure.

Within the range of the inventive compounds, those polyacrylate esters with quaternary ammonium groups are especially preferred, which are obtained by the transesterification of methyl polyacrylate esters with dimethyl- or diethylaminoethanol, 20 to 50% of the ester groups being transesterified, and subsequent quaternization with methyl chloride.

Particularly preferred inventive polyacrylate esters with quaternary ammonium groups are those with an average molecular weight of about 1,000 to 50,000.

In contrast to the copolymers obtained according to the state of the art by the copolymerization of acrylate esters or acrylate ester derivatives with quaternary ammonium groups, the inventive polymers have a more uniform structure. The content of low molecular weight fractions is reduced quite substantially. The inventive copolymers have no toxic or other physiologically harmful properties.

A further aspect of the invention is the use of the inventive polymers in cosmetic preparations. Such use becomes possible only because the compounds are tolerated well. The polymers are particularly suitable as additives in preparations for the care of the hair. Already when used in low concentrations of 0.2 to 2% by weight of the preparation, the inventive polymers improve the combability of the hair, especially of the wet hair, and reduce the static charge on the hair.

A further preferred use of the inventive compounds is in the area of textile auxiliaries. They can be used there as antistatic agents for finishing textile fibers and textile products, such as woven, knitted or nonwoven fabrics and to improve the handle. Since products, so finished, come into contact with the human body, it is also of advantage here that the inventive compounds are physiologically safe.

EXAMPLE 1

Preparation of Polymethyl Acrylate by the Free Radical Polymerization

Not of the Invention

A solution of 0.6 g of azodiisobutyronitrile and 20.2 g of dodecylmercaptan in 50 g of toluene and 280 g (approximately 3.25 moles) of methyl acrylate is added over a period of 2 hours to a reactor containing 53 g of toluene at 100° C. and under an atmosphere of nitrogen. After that, a further 0.9 g of azodiisobutyronitrile, dissolved in 20 g of methyl ethyl ketone, are added over a period of 0.5 hours. Finally, the reaction mixture is kept at 100° C. for 1 hour. At the end of the reaction, the solvent is distilled off. A colorless, viscous liquid with a refractive index of 1.480 remains behind. Gel chromatographic analysis reveals that the polymer obtained has a number average molecular weight $\overline{M}_n$ of 1,950 and a weight average molecular weight $\overline{M}_w$ of 3,330. The nonuniformity coefficient therefore is 1.71. The residual monomer content is 0.1.%.

EXAMPLES 2 and 3

Preparation of Polymethyl Acrylates of Higher Molecular Weight by Free Radical Polymerization Not of the Invention The method of Example 1 is followed, with the exception that the dodecylmercaptan content is lowered. The number average and weight average molecular weights are shown as a function of the dodecylmercaptan content in Table 1.

TABLE 1

| Polymethyl acrylate from Example | Dodecyl-mercaptan (weight %) | Molecular (weight %) $\overline{M}_n$ | Molecular Weight $\overline{M}_w$ | Nonuniformity Coefficient |
| --- | --- | --- | --- | --- |
| 2 | 2.95 | 4,453 | 11,346 | 2.55 |
| 3 | 0.43 | 16,750 | 68,500 | 4.09 |

EXAMPLE 4 A

Transesterification of Polymethyl Acrylate with Diethylaminoethanol

The polymethyl acrylate of Example 1 (184.6 g), dissolved in 185 g of toluene, is heated together with 46.9 g (approximately 0.4 moles) of diethylaminoethanol under nitrogen to 120° C. At first, any traces of water present are removed by azeotropic distillation. After that, 0.8 g of sodium methylate are added as transesterification catalyst. The methanol, which is formed by the transesterification, is separated from the toluene by fractionation. After 2 hours and after 4 hours, an additional 0.7 g of sodium methylate are added. The reaction is ended after about 6 hours; the end of the reaction is indicated by a stillhead temperature of 110° C.

The amount of diethylaminoethanol, determined by gas chromatographic analysis, corresponds to a conversion during the transesterification of 97.5%; the conversion, calculated from the methanol content of the distillate, is 96.2%.

EXAMPLE 4 B

Quaterniazation of Polyacrylate Containing Diethylaminoethyl Groups

Isopropanol replaces toluene as solvent in the product obtained from Example 4 A. The polymer (200 g), diluted 1 : 1 by weight with the solvent, is heated under nitrogen to 110° C. The pressure is adjusted to 3.5 to 4 bar by passing in methyl chloride and kept constant at this value during the reaction by passing in additional methyl chloride.

From the determination of the chloride content and the amine number, it is calculated that a conversion of 98.1 or 99.1% respectively was achieved in the quaternization reaction.

EXAMPLES 5 A-15 A

Transesterification of Polymethyl Acrylates of Different Molecular Weights with Different Dialkylaminoalkanols The procedure of example 4A is followed with the exception that different dialkylaminoalkanols are used in varying molecular ratios with respect to the methyl ester groups. In some cases, isopropyl titanate is used as catalyst instead of sodium methylate. The reaction yields, calculated from the amount of methanol set free and from the amine number, as well as the nature and amount of the dialkylamionoalkanol and catalyst are given in Table 2.

TABLE 2

| | | | | | Conversion | |
| --- | --- | --- | --- | --- | --- | --- |
| Example No. | Polymethyl Acrylate ($M_n$)/Amount (g) | Dialkylamino- alkanol Type/Amount (g) | Catalyst Type/ Amount (g) | Theoretical Degree of Substitution* (%) | From The Amount of Methanol (%) | From The Amine Number (%) |
| 5 A | 1,950/184.6 | DEAE/46.9 | NAM/2.2 | 20 | 96.2 | 97.5 |
| 6 A | 1,950/184.6 | DEAE/93.8 | NAM/4.4 | 40 | 95.6 | 94.8 |
| 7 A | 1,950/184.6 | DEAE/140.6 | NAM/6.5 | 60 | 92.8 | 93.4 |
| 8 A | 1,950/184.6 | DMAE/71.3 | NAM/4.4 | 40 | 96.5 | 95.8 |
| 9 A | 1,950/184.6 | DBAE/140.6 | NAM/4.4 | 60 | 94.3 | 94.0 |
| 10 A | 1,950/184.6 | DMADG/133.2 | NAM/4.4 | 50 | 97.3 | 96.2 |
| 11 A | 1,950/194.6 | DEAE/93.8 | IPT/4.0 | 40 | 97.6 | 96.8 |
| 12 A | 1,950/184.6 | DEAE/117.2 | IPT/4.8 | 50 | 96.8 | 95.2 |
| 13 A | 4,453/177.4 | DEAE/93.8 | IPT/4.0 | 40 | 96.5 | 95.5 |
| 14 A | 16,750/173.0 | DEAE/93.8 | IPT/4.0 | 40 | 94.6 | 93.8 |
| 15 A | 16,750/173.0 | DEAE/140.6 | IPT/5.9 | 60 | 93.2 | 91.9 |

*Theoretical Degree of Substitution = $\dfrac{\text{Number of Substituted Ester Groups}}{\text{Number of Ester Groups Originally Present}}$ Key for Table 2
DEAE = diethylaminoethanol
DMAE = dimethylaminoethanol
DBAE = dibutylaminoethanol
DMADG = diemthylaminodiethylene glycol
NAM = sodium methylate
IPT = isopropyl titanate

EXAMPLES 5 B-17 B

The procedure of Example 4 B is repeated with the exception that the transesterification products 5 A-15 A and, in some cases, benzyl chloride are used for the quaternization. The results of the quaternization of the transesterification products from Examples 5 A–15 A are shown in Table 3 by means of the chloride values and the amine numbers.

TABLE 3

| Example No. | Transesterification Product from Example No. | Quaternizing Agent Type/Amount (g) | Solvent | Yield Chloride Value (%) | Yield Amine Number (5) |
|---|---|---|---|---|---|
| 5 B | 5 A | MC/9.3 | IPA | 97.7 | 99.4 |
| 6 B | 6 A | MC/16.0 | IPA | 97.1 | 99.1 |
| 7 B | 7 A | MC/21.2 | IPA | 97.2 | 99.5 |
| 8 B | 8 A | MC/17.6 | IPA | 98.2 | 99.6 |
| 9 B | 9 A | BC/44.0 | IPA | 94.2 | 98.4 |
| 10 B | 10 A | MC/21.2 | IPA | 89.8 | 91.2 |
| 11 B | 11 A | BC/44.3 | PD | 96.8 | 99.3 |
| 12 B | 12 A | MC/19.6 | PD | 93.4 | 96.2 |
| 13 B | 13 A | MC/19.6 | IPA | 92.6 | 94.3 |
| 14 B | 14 A | MC/16.7 | PD | 92.3 | 94.9 |
| 15 B | 15 A | MC/16.0 | IPA | 96.5 | 95.6 |
| 16 B | 15 A | MC/16.4 | IPA | 95.2 | 97.2 |
| 17 B | 15 A | MC/22.0 | PD | 94.6 | 96.1 |

Key for Table 3:
IPA = isopropyl alcohol;
PD = 1,2-propanediol;
MC = methylchloride;
BC = benzylchloride

EXAMPLE 18

Preparation of a Polymer Containing Quaternary Groups, by Free Radical Copolymerization Not of the Invention A solution of 0.6 g of azodiisobutyronitrile and 20.2 g of dodecylmercaptan in 93.6 g (approximately 1.09 moles) of methyl acrylate, 186.2 g (approx. 1.09 moles) of diethylaminoethyl acrylate and 50 g of toluene is added over a period of 2 hours to a reactor filled with 53 g of toluene at a temperature of 100° C. and under an atmosphere of nitrogen. After that, a further 0.9 g of azodiisobutyronitrile in 20 g of methyl ethyl ketone are added over a period of 0.5 hours. Finally the reaction mixture is added for 1 hour at a constant temperature of 100° C. At the end of the reaction, the solvent and the unreacted monomers are removed by distillation.

The results of a gel chromatographic analysis reveal that the polymer obtained has a number average molecular weight $\overline{M}_n$ of 1670 and a weight average molecular weight $\overline{M}_w$ of 3720. The nonuniformity coefficient accordingly is 2.2. The residual monomer content was determined to be 0.1%.

To begin with, the product obtained is diluted with 300 g of isopropanol and heated under nitrogen in a pressure vessel to 110° C. Enough methyl chloride is then introduced, so that a pressure of 3.5 to 4 bar is obtained. This pressure is maintained constant during the reaction by passing in more methyl chloride. The duration of the reaction is about 5 hours.

From the determination of the chloride content and the amine number, the conversion during the quaternization is found to be 97.9 or 99.0% respectively.

The gel phase chromatogram has a peak in the low molecular weight region, which indicates the presence of low molecular weight fractions.

APPLICATION EXAMPLES

Preparation and Testing of Hair Treatment Agents Using the Transesterification Products With Quaternary Groups Produced in Examples 13 B or 6 B Conditioning shampoo

| | | |
|---|---|---|
| A | Tego ® betaine L7[1] | 2% by weight |
| | Antil ® 141 liquid[2] | 3% by weight |
| B | Transesterification product from Example 13 B | 0.5% by weight |
| C | Sodium lauryl ether sulfate | 10% by weight |
| D | Water | 84.5% by weight |

For the preparation of hair treatment agents, the components are added together in the order given (A to D). Each mixture must have formed a clear solution before the next component is added 1) Tego ® betaine L7 = cocamidopropyl betaine (1-alkoylamino-3-di-methyl-ammonium-propane-3-carboxymethyl-betaine)

2) Anti ® 141 liquid is a liquid thickener based on a nonionic fatty acid ester of polyalkylene glycol.

Cream Rinse

| | | |
|---|---|---|
| A | Teginacid ® X[3] | 6.0% by weight |
| | Cetyl alcohol | 0.5% by weight |
| B | Transesterification product from Example 6 B | 1.0% by weight |
| | Water | 92.5% by weight |

To produce the preparation, A and B are added together at 70° C., homogenized and cooled with stirring.

3) Teginacid ® X is an O/W emulsifier, which is based on a mixture of glycerin monostearates and distearates with polyglycol fatty alcohol ethers.

In the practical application involving a half-side comparison test on human hair, the results reveal
a higher antistatic effect
an improved wet combability
a slight or hardly noticeable "heaviness" of the hairdo
an improved gloss of the hair
in comparison to shampoo formulations or cream rinses with quaternary compounds of the state of the art.

We claim:

1. A polyacrylate ester having quaternary ammonium groups, said ester being the transesterification product of
   (a) an alkyl polyacrylate ester, obtained by free radical polymerization, the alkyl groups of which contain 1 to 8 carbon atoms, with
   (b) a compound of the general formula

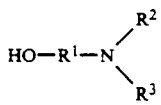

wherein
   $R^1$ is a bivalent group of the general formula

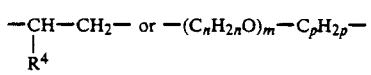

which
   $R^4$ is hydrogen or an alkyl group with 1 to 16 carbon atoms,
   n=2, 3 or 4,
   m=1 to 20,
   p=2, 3 or 4 and
   $R^2$, $R^3$ are alkyl groups with 1 to 18 carbon atoms,
   the transesterification being performed
   (i) in such amounts that up to 70% of the ester groups are transesterified,
   (ii) in the presence of a transesterification catalyst, and
   (iii) in the presence of a solvent,
   whereby a polyacrylate ester with tertiary amino groups is formed as an intermediate, and
   (c) subsequent quaternization of the intermediate with alkyl or alkylaryl halide of the general formula $R^5X$ wherein
   $R^5$ is an alkyl group with 1 to 4 carbon atoms or a benzyl group and
   X is a halogen atom,
   or with dimethyl or diethyl sulfate, at normal or elevated pressure.

2. A polyacrylate ester as claimed in claim 1, wherein (a) is methyl polyacrylate and (b) is dimethyl- or diethylaminoethanol, said alcohol being employed in such amounts that 20 to 50% of the ester groups of (a) are transesterified, the subsequent quaternization (c) being carried out with methyl chloride.

3. A polyacrylate esters as claimed in claim 1 or 2, which has an average molecular weight of 1,000 to 50,000.

4. A polyacrylate ester as claimed in claim 1, wherein the transesterification is carried out at a temperature of between about 70° to 140° C. while the quaternization is performed at a temperature of about between 20° to 140° C.

* * * * *